United States Patent [19]

Block et al.

[11] Patent Number: 5,830,883
[45] Date of Patent: Nov. 3, 1998

[54] METHODS OF CREATING A UNIQUE CHITOSAN AND EMPLOYING THE SAME TO FORM COMPLEXES WITH DRUGS, DELIVERY OF THE SAME WITHIN A PATIENT AND A RELATED DOSAGE FORM

[75] Inventors: Lawrence H. Block; Shobhan S. Sabnis, both of Pittsburgh, Pa.

[73] Assignee: Duquesne University of the Holy Ghost, Pittsburgh, Pa.

[21] Appl. No.: 544,428

[22] Filed: Nov. 6, 1995

[51] Int. Cl.$^6$ .......................... A61K 31/73; A61K 9/22; A61F 13/00

[52] U.S. Cl. .................... 514/55; 604/890.1; 604/891.1; 424/422; 424/423; 424/424; 424/425

[58] Field of Search .......................... 514/55; 604/890.1, 604/891.1; 424/422, 423, 424, 425

[56] References Cited

U.S. PATENT DOCUMENTS

| 3,847,897 | 11/1974 | Dunn et al. | 536/20 |
| 4,286,087 | 8/1981 | Austin et al. | 536/20 |
| 4,532,321 | 7/1985 | Castle et al. | 536/20 |

FOREIGN PATENT DOCUMENTS

2134745  5/1995  Canada.

OTHER PUBLICATIONS

Paul et al. *Journal of Materials Science Letters* 1995, 14, 1792–1794.

Muzzarelli *Polymer Science and Technology* 1983, 23, 359–74.

Lambrecht et al. *Transaction–American Society for Artificial Internal Organs* 1981, 27, 380–385.

Sannan et al., Studies on chitin:7 I.r. spectroscopic determination of degree of deacetylation, Polymer 19, pp. 458–459 (1978).

Miyazaki et al., The Use of Chitin and Chitosan as Drug Carriers, 29(10), Chem. Pharm. Bull., pp. 3067–3069 (1981).

Mima et al., Highly Deacetyland Chitosan and its Properties, J. Appl. Polym. Sci., vol. 28, pp. 1909–1917 (1983).

Domszy et al., Evaluation of Infrared Spectroscopic Techniques for Analyzing Chitosan, Makromol. Chem. 186: pp. 1671–1677 (1985).

Shiraishi et al., Enhancement of Dissolution Rates of Several Drugs by Low–Molecular Chitosan and Alginate, Chem. Pharm. Bull. 38(1), pp. 185–187 (1990).

Imai et al., Interaction of indomethacin with low molecular weight chitosan, and improvements of some pharmaceutical properties of indomethacin by low molecular weight chitosans, Int'l. Jour. of Pharm., pp. 11–20 (1991).

Sawayanagi et al., Use of Chitosan for Sustained–release Preparations of Water–soluble Drugs, Chem. Pharm. Bull 30(11), pp. 4213–4215 (1982).

Chinese Journal of Chinese Universities, vol. 13, No. 7, pp. 1008–1009 (1992) (Handwritten translation enclosed).

*Primary Examiner*—Kathleen K. Fonda
*Attorney, Agent, or Firm*—Arnold B. Silverman; Eckert Seamans Cherin & Mellott, LLC

[57] ABSTRACT

A method of creating a unique deacetylated, depolymerized chitosan which may be employed to provide a time release chitosan-drug complex. The chitosan is deacetylated at least 60 percent and preferably at least 70 percent. It is preferred to employ a chitosan having a molecular weight of about 3.5 kDa to 250 kDa and preferably about 3.5 kDa to 75 kDa. The complex may be employed in various delivery systems including tablets, films, matrix supported drug delivery units or as coatings or films on implants. A method of making a drug delivering implant includes providing an implant, creating a complex of a depolymerized chitosan and a drug and establishing a layer of a chitosan drug complex on at least a portion of said implant. The chitosan-drug complex is preferably created through ionic bonding and may be a coating or a film self-adhered to a portion of an exterior surface of the implant. It is also preferred to deacetylate the chitosan prior to depolymerization. The layer of the chitosan-drug complex is characterized by a prolonged drug time release property as compared with complexes made from polymerized chitosan. A corresponding method of providing drug delivery to the locale of the implant within a patient is disclosed as is the implant.

48 Claims, 1 Drawing Sheet

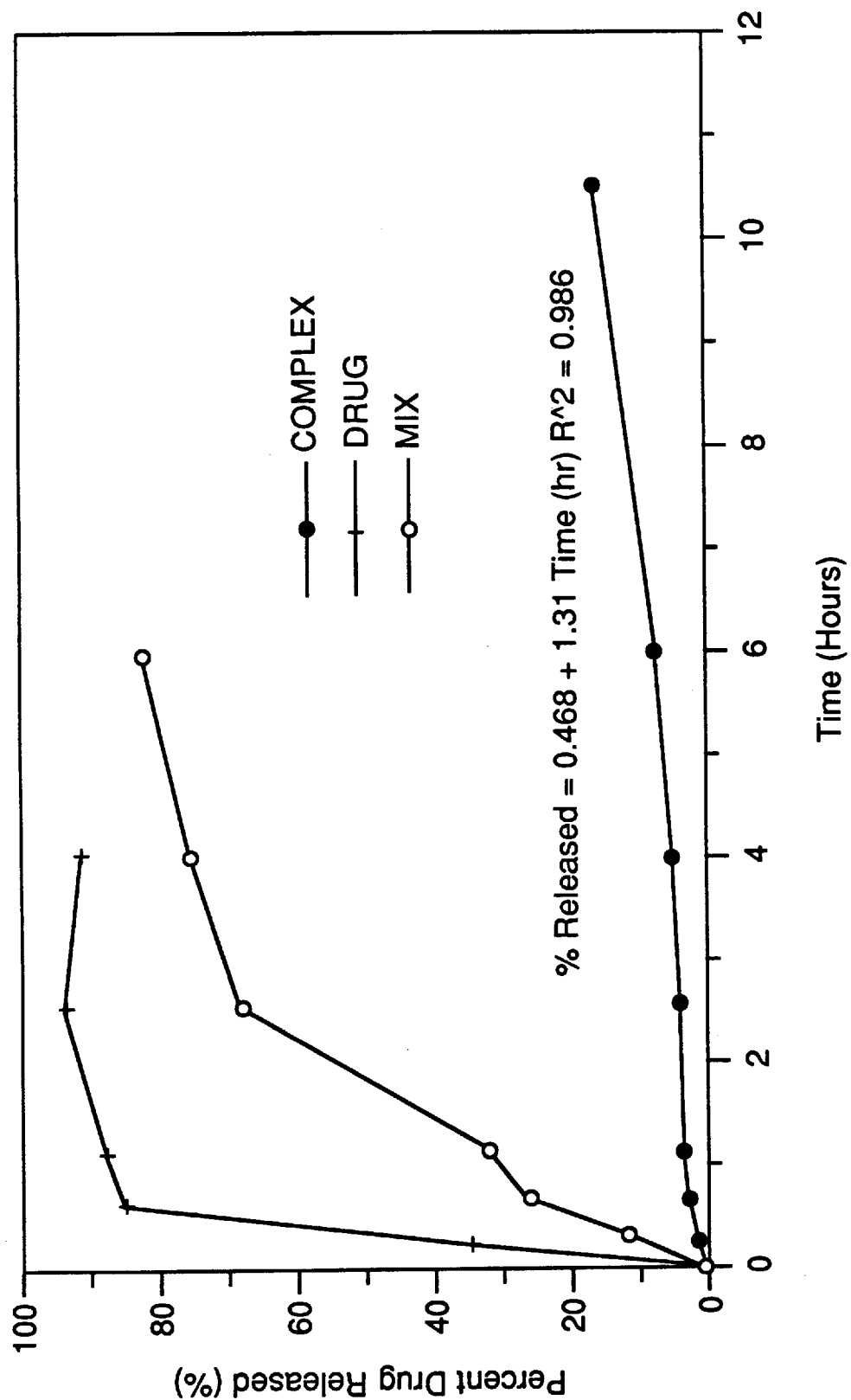

METHODS OF CREATING A UNIQUE CHITOSAN AND EMPLOYING THE SAME TO FORM COMPLEXES WITH DRUGS, DELIVERY OF THE SAME WITHIN A PATIENT AND A RELATED DOSAGE FORM

BACKGROUND OF THE INVENTION

1. Field of the Invention

This invention relates to a method of creating a unique chitosan and the use of such chitosans to form complexes with drugs to provide a drug delivery system. The present invention also relates to a method of making an implant which has enhanced efficiency of drug delivery in the specific location of an implant as a result of the use of a deacetylated, depolymerized chitosan-drug complex, as well as the related implant and the corresponding procedure for delivering the drug and implant within a patient.

2. Description of the Prior Art

As medicine has advanced in recent decades, numerous uses of synthetic prosthetic devices, including implants, have been known. One of the problems with the use of such implants is the exposure of the patient to risk of infection and other medical problems, such as pain and joint inflammation.

It is known that the physico-chemical properties, such as solubility and reactivity of chitosan, can be improved by N-deacetylation of chitin and chitosan.

U.S. Pat. No. 3,847,897 discloses the creation of a thixotropic thickener and a stabilizer made from chitin. It discloses the use of chitin for its resistance to severe food processes. The chitin may be in the form of a microcrystalline chitin in an aqueous stable thixotropic dispersion.

U.S. Pat. No. 4,286,087 discloses a method of making microcrystalline chitin powder. The molecular weight is said to be in the range of about 5,000 to 450,000.

While, in general, the use of medications which are delivered through the bloodstream has been effective for numerous conditions, the risk of infection is not adequately precluded through bloodstream delivery of drugs when there is clot formation or trauma to an affected area. As a result, there remains a need for an improved system which will effect more direct and immediate delivery of a drug in the locale where it is needed in connection with surgical implants.

There is also a need for improved drug delivery systems which involve oral administration of drugs by swallowing or positioning within the oral cavity or topical application.

There is also the problem that local delivery, in the context of implants, must be provided over a sustained period of time and, therefore, control of time release of medication is of great importance.

SUMMARY OF THE INVENTION

The present invention has met the hereinbefore described needs.

The chitosan employed in the present invention is preferably at least 60 percent deacetylated and preferably depolymerized to a molecular weight of about 3.5 to 250 kiloDaltons (kDa).

The invention provides, in one embodiment, a method of making a drug delivering implant, which includes providing an implant, creating a complex of a depolymerized chitosan and a drug, and providing a layer of the chitosan-drug complex on at least a portion of the implant. The complex is preferably created by ionically bonding the depolymerized chitosan to the drug.

The drug may be an antibiotic or an anti-inflammatory, for example. The locally deliverable drug-containing complex may be self-bonded to an implant outer surface and has improved or extended drug time delivery properties as compared with complexes made from polymeric chitosan.

A related implant is also provided as is a method of introducing the implant at least partially into the patient in order to provide the desired local time release delivery of the drug.

The present invention also contemplates the creation of a more reactive and useful chitosan material, as well as the use of the same in creating complexes with drugs and effecting delivery of such drugs.

It is an object of the present invention to provide an enhanced efficiency drug delivery system which is adapted to provide time release delivery of a drug within a patient.

It is a further object of the present invention to provide such a system which may employ a depolymerized chitosan which is ionically bonded to a drug secured to an implant.

It is yet another object of the present invention to provide a lengthened period of drug delivery with respect to prior art systems.

It is a further object of the present invention to provide a drug delivery system wherein the drug has high solubility within the layer containing the same on the implant.

It is an object of the present invention to provide a highly reactive, deacetylated, depolymerized chitosan.

It is a further object of this invention to provide a method of delivering drugs and a drug form including a unique chitosan-drug complex.

These and other objects of the present invention will be more fully understood from the following detailed description of the invention on reference to the illustration appended hereto.

BRIEF DESCRIPTION OF THE DRAWING

The FIGURE is a plot of comparative data of time of release versus percentage of drug released.

DESCRIPTION OF THE PREFERRED EMBODIMENTS

As used herein, the term "patient" shall refer to members of the animal kingdom, including human beings.

The term "ionic bonding," "ionically bonded" or "ionically bonding" as employed herein shall refer to ionic or electrostatic interaction between chitosan and a drug as the sole or principal means for creating the chitosan-drug complex.

The term "implant" as employed herein, refers to (a) synthetic or natural body parts adapted to be invasively or partially invasively introduced into the body of a patient either as a generally permanent or temporary substitute for a body part or (b) a therapeutic aid which may be withdrawn or replaced and shall expressly include, but not be limited to synthetic or natural replacements for body organs, cells, tissue, prostheses, and diagnostic and therapeutic equipment including, but not limited to catheters, cannulas of intravenous medication or nourishment delivering systems and pacemakers.

The term "drug delivery unit" refers to a depolymerized chitosan-drug complex in tablet, film, matrix, microsphere or microcapsule form, either in independent form, or employed as a component to provide a means for drug delivery.

Chitosan is derived from chitin, which is a homopolysaccharide. The repeating unit of the chitin polymer is 2-N acetyl glucosamine. While chitin is insoluble in most solvents, its partially deacetylated derivative "chitosan" is readily soluble in acidic solutions.

Early efforts by the present inventors to mix an acetic acid solution of chitosan with an antibiotic from the cephalosporin generic group, i.e., cefamandole resulted in immediate formation of a voluminous gummy precipitate which was the chitosan-antibiotic complex. The lack of solubility, volume and texture of this complex were both undesirable and unexpected. Also, the ability of the complex to release the antibiotic was less than desirable in that the antibiotic release from the complex was too rapid.

In order to establish a chitosan with increased N-amino substitutions, one may deacetylate the parent polymer chitin by treating the polymer with a 47 to 50 percent w/v sodium hydroxide solution in the manner disclosed in accordance with Mima et al., Highly Deacetylated Chitosan and its Properties, J. Appl. Polym. Sci., 28: pp. 1909–1917 (1983); Sannan et al., Studies on Chitin:7 I.R. Spectroscopic Determination of Degree of Deacetylation, Polymer, 19: pp. 458–459 (1978); Domszy et al., Evaluation of Infrared Spectroscopic Techniques for Analyzing Chitosan, Makromol. Chem. 186: pp. 1671–1677 (1985).

The present inventors have determined that there is a generally linear relationship between the increase and the degree of deacetylation and the square root of deacetylation reaction time. The reaction rate increases with increasing temperature up to about 80° C. Above that temperature, chitosan degrades rapidly into water soluble fractions.

It has been known previously to modify chitosan or chitin to prepare low molecular weight chitosans. See, U.S. Pat. No. 4,286,087 wherein there is disclosed a method of preparing depolymerized chitin (molecular weight equal 33,000) by acid hydrolysis of chitin using phosphoric acid. U.S. Pat. No. 3,847,897 discloses using hydrochloric acid to yield a stable thixotropic dispersion in water. Low molecular weight chitosan has been disclosed as enhancing the dissolution rates and drug release of several drugs. By contrast, the present invention employs the deacetylated, depolymerized chitosan to achieve a chitosan-drug complex which retards and controls drug release to provide a time release of the drugs. See, S. Shiraishi et al., "Enhancement of dissolution rates of several drugs by low-molecular chitosan and alginate," Chem. Pharm. Bull. 38:185–187 (1990); T. Imai et al., "Interaction of indomethacin with low-molecular weight chitosan and improvements of some pharmaceutical properties of indomethacin by low-molecular weight chitosans," Int. J. Pharm. 67: 11–20 (1991). In these papers by S. Shiraishi, the chitosans are reported as having had molecular weights between 3.8 and 25 kDa. but these articles teach the use of low molecular weight chitosans to enhance solubility and drug release rather than to retard drug release or control it. In effect, our use of low molecular weight chitosans is contrary to the prior art because the present invention proposes that these materials can be used to limit drug release.

One embodiment of the present invention includes a method of making a drug delivering implant which includes providing an implant, creating a complex of a depolymerized chitosan and a drug in an appropriate acidic solution, preferably having a pH of 3 or less. Acids such as acetic acid or hydrochloric acid are suitable for this purpose. A layer of the chitosan drug complex is then provided on at least a portion of the implant. The complex will generally be created by ionically bonding the depolymerized chitosan to the drug. The layer may be provided as a coating or as a preformed film which is secured to at least a portion of the implant and generally to an exterior surface thereof. The layer is preferably a self-adhering layer. The depolymerized chitosan will have a molecular weight of about 3.5 to 250 kDa and will preferably have a molecular weight of about 3.5 kDa to 75 kDa. The layer secured to the implant may be of any desired thickness to serve the purpose. For example, in some instances, the coating thickness may be about 0.01 to 0.30 cm and preferably 0.20 to 0.30 cm. Prior to depolymerization of the chitosan, deacetylation of the same is preferably effected in a preferred embodiment. The chitosan will preferably be deacetylated by about at least about 60 percent and most preferably at least about 70 percent. If the chitosan is deacetylated less than about 60 percent, the chitosan will have reduced solubility and, therefore, be less reactive. The deacetylation of the chitosan serves to enhance reactivity. It increases the number or availability of the reactive amino groups within the polymer and thereby facilitates ionic interaction with drugs to facilitate creation of the chitosan drug complex. By contrast, prior art use of deacetylation was primarily to increase aqueous solubility.

In a preferred practice of the present invention, the depolymerized chitosan is prepared as a microcrystalline powder rather than as an aqueous slurry as prepared in the prior art. The microcrystalline powder will preferably have a particle size of about 75 $\mu$m to 425 $\mu$m.

Example 1

This is an example of the preparation of a depolymerized chitosan of the present invention. The preferred process involves acid hydrolysis of chitosan, followed by application of agitation to establish shear stress with the resultant dispersion being dried about 60° C. for about 72 hours, followed by milling and sieving to obtain fine microcrystalline chitosan. In the preferred practice of the invention, the acid digestion process may employ hydrochloric acid in the range of 0.8 to 2.5 M with the molecular weight of the product being controlled by varying the acid treatment time, i.e., digestion time. Increasing the reaction time from about 0.5 to 2 hours, produced chitosans with molecular weights of about 75 to 3.5 kDa, respectively, as compared with the starting material which had a molecular weight of approximately 580 kDa. Shear was applied employing a Lightnin'mixer at about 500 to 1800 rpm for about 3 to 15 minute time periods. After the shearing action, the resultant dispersion was dried at about 60° C. for 72 hours, followed by milling and sieving to obtain a fine microcrystalline powder.

The depolymerized chitosan of the present invention is to be distinguished from prior art depolymerized chitosan obtained by fractionation, i.e., separating the lower molecular weight fractions from higher molecular weight fractions. The preferred depolymerization of the present invention is primarily a chemical depolymerization as distinguished from fractionation.

It will be appreciated from the foregoing that the present invention provides a unique chitosan and a locally available drug delivery, such as an anti-infective agent which, for example, may be an antibiotic, such as a cephalosporin which, for example, may be cefamandole, cefazolin, cefoxitin, ceftriaxone, or a penicillin, or other medications, such as anti-cancer compounds or an anti-inflammatory which, for example, may be diclofenac, ibuprofen, flurbiprofen, or any other drug which will function in a non-toxic manner and be capable of ionic bonding. The invention may also be employed with drugs for osteoporosis, such as etidronate phosphate. The anti-infective agent, rifampin may also be used.

Depending upon the nature of the implant, one would normally coat or apply a film to a portion or substantially all of the exterior or exposed surfaces which will come into most intimate contact with adjacent body parts. For example, the exterior of a catheter, an intravenous cannula or a pacemaker type device may be fully coated. By pre-applying the cross-linked chitosan-drug complex to the implant, the medication would automatically be provided in the region of the implant and will be delivered in the desired time sequence.

The implant of the present invention may have a layer of depolymerized chitosan ionically bonded to a drug which layer is self-adhered to the implant. The implant has the property of prolonged time delivery of the drug as compared with a corresponding chitosan complex made from non-depolymerized chitosan. Depolymerization of chitosan to a molecular weight of about 3.4 to 250 kDa renders the aqueous solutions less viscous and the powders more compressible and free flowing.

Example 2

In order to provide an enhanced understanding of a preferred method of combining the deacetylated, depolymerized chitosan of the present invention with a drug to create a chitosan drug complex, an example will be provided.

Deacetylated (87%) depolymerized chitosan (4 g), prepared by the method described herein, is dissolved in approximately 100 mL of 2 percent (v/v) acetic acid solution to yield a 4 percent w/v chitosan solution. Six grams of the antibiotic cefamandole sodium is dissolved in approximately 30 mL of distilled water to yield a solution containing 200 mg of drug per mL. This drug solution is added dropwise to the chitosan solution while stirring. Stirring is continued for 10 minutes. The precipitated complex is recovered by filtration and the precipitate is washed repeatedly with distilled water (until there is no evidence of the drug in the washings). The complex is dried at room temperature in vacuo for 24 hours. The particle size of this dried complex is reduced by grinding at low shear, such as in a mortar and pestle. Using chitosan with a molecular weight of 12 kDa, the chitosan:drug ratio of the complex prepared in this manner was 1.2. Chitosan with a molecular weight of 4 kDa yielded a complex with a chitosan:drug ratio of 1:1.7. This example provides evidence of the increased reactivity of the chitosan as the degree of polymerization decreases.

In view of the adhesive properties of chitosan solutions, one could disperse the microcrystalline chitosan in acetic acid and then dip a solid, such as an implant into the solution repeatedly to build up a layer of film of the polymer. This polymer coated solid could then be dried and the resultant film of chitosan on the solid surface would interact with the drug when dipped into a drug solution to form the chitosan-drug complex as an adherent layer or film.

Example 3

The depolymerized chitosan of the present invention was compared with prior art chitosans to determine physical and chemical modifications. The results of the comparative evaluations are shown in the Table.

TABLE

| | | Slope | Intercept | Molecular Weight (kDa) | Compressibility (%) |
|---|---|---|---|---|---|
| A | Prior Art Chitosan I | 60.99 | 10.30 | 579 | 4.3 |
| B | Prior Art Chitosan II | 53.13 | 7.20 | 307 | 6.8 |
| C | Prior Art Chitosan III | 92.44 | 9.877 | 541 | N/A |
| D | Depolymerized Powdered Chitosan | 0.419 | 0.81 | 6.1 | 19 |

Sample A is the Sigma chitosan from which Sample D of the present invention was made. Sample B is a Fluka low molecular weight prior art sample and Sample C is a Fluka high molecular weight prior art sample. It is seen that the depolymerized chitosan of the present invention has a lower molecular weight and has a different physical behavior as exemplified by the marked difference in compressibility. Also, the slope and intercept values of the viscosity concentration data confirm that the depolymerized chitosan of the present invention is less viscous than the others in the table.

In order to test the time release capabilities of the present complex, a tablet of the complex was placed in water using USP type II apparatus. For comparison (a) tablets of the free drug and (b) a physical mixture of the chitosan polymer and the same drug with the loading being the same as the complex were also tested. Drugs were placed in die cavities with only a single surface of each tablet exposed and one of the sides of the die was sealed off by wax. As shown in the FIGURE in respect of time release characteristics, the drug in tablet form had released over 90 percent of the 80 milligrams of cefamandole sodium in less than 3 hours. The mixture of cefamandole and chitosan in a 1.19:1 ratio had released about 80 percent of the drug within 6 hours. By contrast, the complex of the present invention, which consisted of a 40 milligram tablet of dried cefamandole and chitosan complex in a 1.19:1 ratio had released less than about 20 percent of the drug after over 10 hours. This confirms the desirable time release characteristics of the depolymerized chitosan complex of the present invention.

The present invention depolymerization results in more reactive groups on the polymer backbone being exposed to the environment in order to increase accessibility of chitosan for complexation with the drug. This is to be contrasted with the chitin macromolecule which exists in the form of random coils, such that a portion of the reactive group remains inaccessible. Further, applicant's depolymerized chitosan not only has decreased molecular weight and increased microcrystallinity, but also has subsequent compressibility and, as a result, improves the potential for solid drug delivery system development. Also, the decrease in molecular weight results in decreased viscosity of the solutions or dispersions of these modified chitosans and, therefore, allows greater ease of filtration, processing, such as mixing and interaction with other process components, such as drugs. Further, the present invention produces enhanced bio-adhesive properties as compared with the unmodified chitosan polymer thereby facilitating self-adhering to synthetic implant materials.

When the chitosan-drug complex is formed, decreased solubility in an aqueous solution results due to the neutralization of the electrical charges providing reduced polarity in the resultant complex. As a result, the less polar complex is less able to associate with the polar water structure, thereby resulting in decreased aqueous solubility.

The depolymerized chitosan of the present invention may be complexed with a wide range of anionic drugs by ionic interaction.

Unlike covalently bonded complexes, ionically bonded complexes do not need chemical or enzymatic hydrolysis for the release of drugs. As a result, greater control of drug release of soluble anionic drugs can be achieved by ionic complexes of the present invention. Also. a much lower energy level is required in disassociating the ionic bonds involved. As a result, drug release is controlled essentially by the solubility of the complex resulting in a predictable constant rate, i.e., zero order release of the drug. The release of a water soluble antibiotic may be on the order of about 1 to 2 percent per hour or even less.

The chitosan-drug complex of the present invention, in addition to being employable with implants, may be employed in other forms. For example, the complex can be shaped, molded, or compressed to provide a tablet or provided on a matrix support in unit or multiple drug delivery unit. If desired, plasticizers or other excipients may be employed. These forms could be inserted into the body of a patient, taken orally or applied topically, for example. The complex could also be sprinkled as a powder on the desired area. The complex could be cast into a film that could be applied to or draped on a surface, The complex preferably can be self-adhered to an implant or body part, if desired.

As chitosans are biodegradable, it will be appreciated that after the drug has been released in a time delayed manner, the chitosan will undergo biodegradation, thereby minimizing any residual effect on the biological environment.

The time release features of the present chitosan-drug complex permits not only insertion and delivery to a targeted area, but also could be employed to release a drug in such a manner to permit delivery by convective transport through blood or lymph system delivery, or diffusive transport, as by interstitial fluid, for example, to the desired site.

While for convenience of reference herein, examples of specific drugs have been provided, it will be appreciated that a wide variety of drugs may be advantageously ionically bonded to the chitosan of the present invention.

It will be appreciated that the present invention will generally provide a non-gelatinous, non-rigid precipitate which could be separated, extracted, dried and processed into the desired form, such as a powder or granular material. This powder or granular material could then be utilized in a drug delivery system in those forms or could be employed in combination with excipients, to create an efficient drug delivery system.

It will be appreciated that the present invention provides a unique new chitosan which is more reactive and by creating a chitosan drug complex provides an effective system for local delivery of drugs in a time release fashion. The system may advantageously be employed in connection with patients receiving implants. A preferred approach is the use of an ionic complex of chitosan and a drug in a self-adhered layer on an implant.

Whereas particular embodiments of the invention have been described herein for purposes of illustration, it will be evident to those skilled in the art that numerous variations of the details may be made without departing from the invention as set forth in the appended claims.

We claim:

1. A method of making a time release drug delivering implant comprising providing an implant, creating a complex of depolymerized chitosan and a drug by ionically bonding said chitosan and drug, and establishing a layer of said chitosan-drug complex on at least a portion of said implant.

2. The method of claim 1 including establishing said layer by coating at least a portion of said implant.

3. The method of claim 1 including establishing said layer by applying a film containing said chitosan-drug complex to said implant.

4. The method of claim 1 including employing an antibiotic as said drug.

5. The method of claim 1 including employing an anti-inflammatory as said drug.

6. The method of claim 1 including employing as said chitosan a chitosan having a molecular weight of about 3.5 kDa to 250 kDa.

7. The method of claim 1 including employing as said chitosan a chitosan having a molecular weight of about 3.5 kDa to 75 kDa.

8. The method of claim 1 including establishing said layer by self-adhering said layer to said implant.

9. The method of claim 1 including prior to depolymerizing said chitosan, deacetylating said chitosan by at least 60 percent.

10. The method of claim 7 including prior to depolymerizing said chitosan, deacetylating said chitosan by at least 70 percent.

11. The method of claim 9 including applying said chitosan-drug layer in an average thickness of about 0.01 to 0.30 cm.

12. The method of claim 1 including establishing by said layer longer time release properties of said drug as compared with polymerized chitosan-drug complexes.

13. The method of claim 1 including employing said chitosan in microcrystalline powder form.

14. The method of claim 12 including said portion of said implant including an external surface thereof.

15. The method of claim 6 including prior to depolymerizing said chitosan, deacetylating said chitosan by at least 70 percent.

16. The method of claim 13 including employing said microcrystalline powder in a particle size of about 75 $\mu$m to 425 $\mu$m.

17. The method of claim 1 including employing a chemical process to depolymerize said chitosan.

18. The method of claim 16 wherein said implant is a synthetic or natural body part.

19. A time release drug delivering implant comprising an implant, a complex of a depolymerized chitosan and a drug disposed on at least a portion of said implant, and said complex being an ionically bonded complex.

20. The implant of claim 19 including said layer being a coating.

21. The implant of claim 19 including said layer being a film secured to at least a portion of said implant.

22. The implant of claim 19 including said drug being an antibiotic.

23. The implant of claim 19 including said drug being an anti-inflammatory agent.

24. The implant of claim 22 including said depolymerized chitosan component of said chitosan-drug complex having a molecular weight of about 3.5 kDa to 250 kDa.

25. The implant of claim 19 including said layer of said chitosan-drug being self-adhered to said implant.

26. The implant of claim 19 including said chitosan component of said chitosan-drug complex being a deacetylated chitosan.

27. The implant of claim 26 including said deacetylated chitosan being at least 60 percent deacetylated.

28. The implant of claim 27 including said chitosan-drug complex layer having a thickness of about 0.01 to 0.30 cm.

29. The implant of claim 19 including said chitosan-drug complex having longer time drug release properties as compared with a nondepolymerized chitosan-drug combination.

30. The implant of claim 19 including said depolymerized chitosan having a molecular weight of about 3.5 to 75 kDa.

31. The implant of claim 29 including said implant being an artificial organ.

32. The implant of claim 29 including said implant being a catheter.

33. The implant of claim 19 including said portion including an external surface thereof.

34. The implant of claim 31 including said chitosan being a chemically depolymerized chitosan.

35. The implant of claim 28 including said deacetylated, depolymerized chitosan having a reduced viscosity in aqueous solutions as compared with chitosans which have a greater molecular weight and are not deacetylated to the same extent.

36. A method of providing time release drug delivery to a patient at the location of an implant comprising providing an implant, creating a complex of a depolymerized chitosan and said drug by ionically bonding said chitosan to said drug, establishing a layer of said chitosan-drug complex on at least a portion of said implant, and introducing said implant into said patient.

37. The method of claim 36 including establishing said layer by coating at least a portion of said implant.

38. The method of claim 36 including establishing said layer by applying a film containing said chitosan-drug complex to said implant.

39. The method of claim 36 including employing an antibiotic as said drug.

40. The method of claim 36 including employing an anti-inflammatory as said drug.

41. The method of claim 39 including employing as said chitosan a chitosan having a molecular weight of about 3.5 kDa to 250 kDa.

42. The method of claim 36 including establishing said layer by self-adhering said layer to said implant.

43. The method of claim 36 including prior to depolymerization of said chitosan, deacetylating said chitosan by at least about 60 percent.

44. The method of claim 43 including employing as said chitosan a chitosan having a molecular weight of about 3.5 to 75 kDa.

45. The method of claim 44 including applying said chitosan-drug layer in an average thickness of about 0.20 to 0.30 cm.

46. The method of claim 36 including establishing by said layer a longer time release property of said drug as compared with nondepolymerized chitosan-drug combinations.

47. The method of claim 46 including said portion including an external surface thereof.

48. The method of claim 36 including employing a chemical process to depolymerize said chitosan.

* * * * *

UNITED STATES PATENT AND TRADEMARK OFFICE
CERTIFICATE OF CORRECTION

PATENT NO. : 5,830,883
DATED : November 3, 1998
INVENTOR(S) : Lawrence H. Block and Shobhan S. Sabnis It is certified that error appears in the above-indentified patent and that said Letters Patent is hereby corrected as shown below:

Cover Page, Other Publications, Mima et al., change "Deacetyland" to -- Deacetylated --.

Signed and Sealed this

Nineteenth Day of October, 1999

Attest:

Attesting Officer

Q. TODD DICKINSON

Acting Commissioner of Patents and Trademarks